(12) United States Patent
Singer (10) Patent No.: US 8,679,744 B2
(45) Date of Patent: Mar. 25, 2014

(54) METHOD FOR CLEANING AND ISOLATING NUCLEIC ACID USING AMMONIUM OR PHOSPHONIUM CATIONIC DETERGENTS

(75) Inventor: Thorsten Singer, Solingen (DE)

(73) Assignee: Qiagen GmbH, Hilden (DE)

( * ) Notice: Subject to any disclaimer, the term of this patent is extended or adjusted under 35 U.S.C. 154(b) by 805 days.

(21) Appl. No.: 11/572,085

(22) PCT Filed: Jul. 15, 2005

(86) PCT No.: PCT/EP2005/007736
§ 371 (c)(1),
(2), (4) Date: Oct. 24, 2007

(87) PCT Pub. No.: WO2006/008090
PCT Pub. Date: Jan. 26, 2006

(65) Prior Publication Data
US 2008/0113348 A1    May 15, 2008

(30) Foreign Application Priority Data
Jul. 15, 2004    (DE) .......................... 10 2004 034 433

(51) Int. Cl.
*C12Q 1/68*    (2006.01)
*B01L 3/00*    (2006.01)

(52) U.S. Cl.
USPC .......................................... 435/6.1; 422/430

(58) Field of Classification Search
USPC .......................................... 435/6.1; 422/430
See application file for complete search history.

(56) References Cited

U.S. PATENT DOCUMENTS

| | | | |
|---|---|---|---|
| 5,234,809 A | 8/1993 | Boom et al. | |
| 5,300,635 A * | 4/1994 | Macfarlane | 536/25.4 |
| 6,762,027 B2 * | 7/2004 | Greenfield et al. | 435/6 |
| 6,797,476 B2 | 9/2004 | Lander et al. | |
| 2002/0151048 A1 | 10/2002 | Lander et al. | |
| 2003/0032147 A1 * | 2/2003 | Sauer et al. | 435/91.1 |
| 2003/0229222 A1 * | 12/2003 | Kojima | 536/25.42 |

FOREIGN PATENT DOCUMENTS

| | | |
|---|---|---|
| EP | 389063 | 3/1990 |
| EP | 616639 | 9/1994 |
| EP | 1 771 562 | 4/2007 |
| WO | WO 00/34463 | 6/2000 |

OTHER PUBLICATIONS

Griffiths et al., Rapid Method for Coextraction of DNA and RNA from Natural Environments for Analysis of Ribosomal DNA and rRNA-Based Microbial Community Composition, Applied and Environmental Microbiology, 0099-2240/00/$04.0010, Dec. 2000, p. 5488-5491.*
STRATAGENE catalog, 1988, p. 39.*
Vogelstein & Gillespie, (1979). Preparative and analytical purification of DNA from agarose. Proc. Natl Acad. Sci., USA, 76, 615-619.
Marko, M.A., Chipperfield, R. And Birnbiom, H.G., (1982). A procedure ofr the large-sclae isolation of highly purified plasmid DNA using alkaline extraction and binding to glass powder. Anal. Biochem., 121, (1982), 382-387.
Sambrook, J., Fritsch, E.F., Maniatis, T. (1989). Molecular Cloning: A Laboratory Manual. 2nd Ed. E3-E4; E10-E11.
Eskilsson et al.; "DNA—Surfactant Complexes At Solid Surfaces"; Langmuir; 2001; vol. 17; p. 1666-1669; American Chemical Society.
Letter from Chaz de la Garza dated Jan. 14, 2013.

* cited by examiner

*Primary Examiner* — Jezia Riley
(74) *Attorney, Agent, or Firm* — Miles & Stockbridge, P.C.

(57) ABSTRACT

The present invention relates to a method for cleaning and isolating nucleic acids using cationic detergents with the general formula (I):

$$Y^+R_1R_2R_3R_4X^- \qquad (I)$$

where
Y can represent nitrogen or phosphorus
$R_1$, $R_2$, $R_3$ and $R_4$ can represent independently from one another an unbranched or branched $C_1$-$C_{20}$-alkyl residue, $C_3$-$C_6$-alkenyl residue, $C_3$-$C_6$-alkinyl residue and/or a $C_6$-$C_{20}$-aryl residue as well as a $C_6$-$C_{26}$-aralkyl residue, and
X— can represent an anion of an inorganic or organic single or multi-basic acid.

23 Claims, 5 Drawing Sheets

METHOD FOR CLEANING AND ISOLATING NUCLEIC ACID USING AMMONIUM OR PHOSPHONIUM CATIONIC DETERGENTS

CROSS REFERENCE TO RELATED APPLICATIONS

This application is 35 USC §371 national stage application of International Application No. PCT/EP05/007736 filed Jul. 15, 2005, which claims priority to German Application No. 102004034433.7 filed Jul. 15, 2004.

BACKGROUND OF THE INVENTION

Methods for isolating nucleic acids are well known from the state of the art. Accordingly, according to one of the most established methods in the state of the art, DNA is isolated from biological starting materials—such as cells and tissues—by solubilising the starting materials containing the nucleic acid under strongly denaturising and reducing conditions (partially also by using protein-degrading enzymes) and isolating the thus released nucleic acids from the aqueous phase by the dialysis method or by means of an ethanol precipitation [J. Sambrock, E. F. Fritsch and T. Maniatis, 1989, Cold Spring Harbor, "Molecular Cloning"].

The main disadvantage of this method is seen in the fact that the isolation of nucleic acids from cells and in particular from tissues has shown itself to be very time-consuming and can frequently take more than two days. In addition, this method necessitates a considerable outlay on apparatus, and includes the use of substances such as phenol or chloroform, which irritate the skin or damage health.

In view of this situation, alternative methods were developed at an early stage in the state of the art, which are intended to enable the disadvantages involved in the extraction of nucleic acids described above to be avoided.

All these methods are based on a method developed and described for the first time by Vogelstein and Gillespie (Proc. Natl. Acad. Sci, USA, 1979, 76, 615-619) for the preparative and analytical cleaning of DNA fragments from agarose gels. The method combines the dissolving of the agarose containing the DNA band to be isolated in a saturated solution of a chaotropic salt (NaJ) with a bonding of the DNA to glass particles. The DNA fixed to the glass particles is subsequently washed with a washing solution (20 mM Tris HCl [pH 7.2], 200 mM NaCl; 2 mM EDTA; 50% v/v ethanol) and then desorbed from the carrier particles.

This methodology has undergone a series of modifications up to today and at the present time is used for different methods of extracting and cleaning nucleic acids of different provenances (Marko, M. A., Chipperfield, R. and Birnboim, H. G., Anal. Biochem., 121, (1982) 382-387).

Accordingly, numerous reagent combinations (so-called kits) are commercially available for carrying out nucleic acid extractions of this kind.

These almost exclusively commercially available kits are based on the sufficiently well-known principle of bonding nucleic acids to mineral carriers under the presence of solutions of different chaotropic salts, and use suspensions of finely ground glass powder (e.g. Glasmilk, BIO 101, La Jolla, Calif.), diatomic earths (Sigma) or even silica gels (European patent application 616 639) as carrier materials.

A method of isolating nucleic acids, which in principle is practical for a large number of different applications, has been disclosed in Boom et al. [EP 389 063 A1]. In this European patent application, a method is described for isolating nucleic acids from starting materials containing nucleic acids by incubating the starting material with a chaotropic buffer of a DNA-bonding solid phase. The chaotropic buffers realise both the lysis of the starting material and also the bonding of the nucleic acids to the solid phase. The method is also suitable for isolating nucleic acids from small sample quantities, and finds practical use particularly in the field of isolating viral nucleic acids.

Although problems, which develop due to a possibly difficult lysis of the starting material, can be solved by a series of commercially available products for the isolation of nucleic acids (especially for the isolation of genomic DNA from complex starting materials), they conceal however the major disadvantage that this is no longer a classic "single tube method", which characterises the above method according to the disclosure of Boom et al., as the lysis of the starting material is carried out in an ordinary buffer using a proteolytic enzyme. The chaotropic ions necessary for the subsequent bonding of the nucleic acids to centrifugation membranes, for example, must be additionally added to the lysis preparation when the lysing is complete. In no circumstances can they form part of the lysis buffer, as the protein-destroying function of chaotropic salts is well known and would naturally immediately destroy the proteolytic enzyme necessary for efficient lysis.

In spite of a series of disadvantages, the methods of nucleic acid isolation using chaotropic salts have become established worldwide and are applied in their millions using commercially available products. These systems are extremely simple in their execution and in all cases proceed in accordance with the following principle:

Lysis of the starting material, subsequent bonding of the nucleic acids to the solid phase of a glass or silica membrane, which is located on a carrier suspension in a centrifuge column;

Washing of the bonded nucleic acids, and

Elution of the nucleic acids with a buffer of low ion strength;

All these systems are based on the bonding of the nucleic acids to the respective carrier surfaces in the presence of chaotropic salts, i.e. at least one buffer solution contains a chaotropic salt as its main component. Under certain circumstances, this can even apply to the lysis buffer or—in systems that use proteolytic enzymes—to a necessary bonding buffer, which is added to the starting material after lysis is complete.

The Hofmeister series for salting out negatively charged, neutral or basic protein solutions forms the basis for the selection of suitable chaotropic salts. Chaotropic salts are characterised by denaturing proteins, increasing the solubility of unpolar substances in water, and destroying hydrophobic interactions. According to the state of the art, just these characteristics also effect the destruction of the superimposed structure of the aqueous environment with buffer systems of chaotropic salts, in order to promote the bonding of the nucleic acids to selected solid phases. The best-known agents for isolating nucleic acids are sodium perchlorate, sodium iodide, potassium iodide, guanidinium-isothiocyanate and guanidinium hydrochloride. However, they are cost-intensive on the one hand and to some extent toxic or irritant on the other.

The physical-chemical principle of the bonding of nucleic acids to mineral carriers in the presence of chaotropic salts has been explained in professional circles. The bonding of nucleic acids to the surfaces of mineral carriers consists in the breaking down of superimposed structures of the aqueous environment, by means of which the nucleic acids adsorb on the surface of mineral materials, in particular of glass or silica particles. The presence of chaotropic ions is always necessary to break down the superimposed structures of the aqueous environment. When the concentrations of the chaotropic salts are high, the reaction proceeds almost quantitatively. As a result of this physical-chemical knowledge that has been described, it is assumed in the state of the art that all commercially available systems for isolating nucleic acids must contain buffer compositions with high ion strengths of chaotropic salts for bonding nucleic acids to a nucleic-acid-bonding solid phase.

In addition, appropriate methods are also known from the state of the art, which manage without the use of chaotropic substances or without the use of phenol, by means of which the disadvantages described above can be avoided. International patent application WO 00/034463 discloses methods of this kind for isolating nucleic acids from complex starting materials. In these methods, a lysing/bonding buffer system is used, which has at least one antichaotropic salt component and works with a so-called alcoholic bonding chemistry (Invisorb® Plasmid Kit produced by Invitek, Berlin).

The use of alcohols, however, also has some disadvantages, which in particular include the following:

Exactly determined volume ratios of sample lysis to alcohol must be maintained meticulously accurately for plasmid isolation in order to prevent contamination of the plasmid to be isolated—in particular with RNA.

Both the chaotropic and the alcoholic bonding chemistry result in DNA isolates, which are strongly contaminated with endotoxins. Additional washing steps are limited to the use of buffers containing large amounts of alcohol in order to be able to maintain the bond to the solid phase—usually a membrane. Selective washing steps, which make the use of other substances necessary, can therefore hardly be used for this purpose.

The endotoxin content in the isolated DNA can lead to problems with the further use of the DNA isolated in this manner—for example in pharmaceutical applications.

SUMMARY OF THE INVENTION

Consequently, the object of the present invention consists in first overcoming the disadvantages of the state of the art described above.

This problem is solved by the use of cationic detergents of the general formula (I) in order to bond the nucleic acids to a solid matrix. Suitable matrices—such as cellulose, for example—are known from the state of the art. According to the invention, however, a silica or glass fibre matrix is preferred.

DETAILED DESCRIPTION OF A PREFERRED EMBODIMENT

The present invention relates to a method for cleaning and isolating nucleic acids using cationic detergents with the general formula:

$$Y^+R_1R_2R_3R_4X^- \quad (I)$$

where

Y can represent nitrogen or phosphorus, $R_1$, $R_2$, $R_3$ and $R_4$ can represent independently from one another an unbranched or branched $C_1$-$C_{20}$-alkyl residue, $C_3$-$C_6$-alkenyl residue, $C_3$-$C_6$-alkinyl residue and/or a $C_6$-$C_{20}$-aryl residue as well as a $C_6$-$C_{26}$-aralkyl residue, and $X^-$ can represent an anion of an inorganic or organic single or multi-basic acid.

Compositions are preferred in which the cationic compounds consist of an ammonia salt, in which $R_1$ represents a higher alkyl residue, preferably with 12, 14, 16 or 18 carbon atoms, and $R_2$, $R_3$ and $R_4$ each represent a methyl group.

Furthermore, compositions are preferred in which $R_1$ represents an aralkyl group, preferably a benzyl group, $R_2$ represents a higher alkyl residue with 12, 14 or 16 carbon atoms, and $R_3$ and $R_4$ represent a methyl group.

As a general rule, $C_1$-$C_6$-alkyl represents a branched or unbranched hydrocarbon residue with 1 to 6 carbon atom(s), which can be substituted if necessary with one or more halogen atom(s)—preferably fluorine—which can be the same as or different from one another.

The following hydrocarbon residues are cited as examples:
Methyl, Ethyl, Propyl, 1-Methylethyl (iso-Propyl), Butyl, 1-Methylpropyl, 2-Methylpropyl, 1,1-Dimethylethyl, n-Pentyl, 1-Methylbutyl, 2-Methylbutyl, 3-Methylbutyl, 1,1-Dimethylpropyl, 1,2-Dimethylpropyl, 2,2-Dimethylpropyl, 1-Ethylpropyl, Hexyl, 1-Methylpentyl, 2-Methylpentyl, 3-Methylpentyl, 4-Methylpentyl, 1,1-Dimethylbutyl, 1,2-Dimethylbutyl, 1,3-Dimethylbutyl, 2,2-Dimethylbutyl, 2,3-Dimethylbutyl, 3,3-Dimethylbutyl, 1-Ethylbutyl, 2-Ethylbutyl, 1,1,2-Trimethylpropyl, 1,2,2-Trimethylpropyl 1-Ethyl-1-methylpropyl and 1-Ethyl-2-methyl-propyl.

Higher alkyl residue represents a branched or unbranched $C_7$-$C_{20}$-alkyl residue, which can be substituted if necessary with one or more halogen atom(s)—preferably fluorine—which can be the same as or different from one another. The following hydrocarbon residues are cited as examples: branched or unbranched Heptyl, Octyl, Nonyl, Decyl, Undecyl, Dodecyl, Tetradecyl, Hexadecyl, Oktadecyl and Eicosyl.

As a general rule, $C_3$-$C_6$-alkenyl represents a branched or unbranched hydrocarbon residue with 3 to 6 carbon atoms with one or possibly more double bonds, which can be substituted if necessary with one or more halogen atom(s)—preferably fluorine—which can be the same as or different from one another.

The following hydrocarbon residues are cited as examples:
2-Propenyl (Allyl), 2-Butenyl, 3-Butenyl, 1-Methyl-2-propenyl, 2-Methyl-2-propenyl, 2-Pentenyl, 3-Pentenyl, 4-Pentenyl, 1-Methyl-2-butenyl, 2-Methyl-2-butenyl, 3-Methyl-2-butenyl, 1-Methyl-3-butenyl, 2-Methyl-3-butenyl, 3-Methyl-3-butenyl, 1,1-Dimethyl-2-propenyl, 1,2-Dimethyl-2-propenyl, 1-Ethyl-2-propenyl, 2-Hexenyl, 3-Hexenyl, 4-Hexenyl, 5-Hexenyl, 1-Methyl-2-pentenyl, 2-Methyl-2-pentenyl 3-Methyl-2-pentenyl, 4-Methyl-2-pentenyl 1-Methyl-3-pentenyl, 2-Methyl-3-pentenyl 3-Methyl-3-pentenyl, 4-Methyl-3-pentenyl, 1-Methyl-4-pentenyl, 3-Methyl-4-pentenyl, 4-Methyl-4-pentenyl, 1,1-Dimethyl-2-butenyl, 1,1-Dimethyl-2-butenyl, 1,1-Dimethyl-3-butenyl, 1,2-Dimethyl-2-butenyl, 1,2-Dimethyl-3-butenyl, 1,3-Dimethyl-2-butenyl, 1,3-Dimethyl-3-butenyl, 2,2-Dimethyl-3-butenyl, 2,3-Dimethyl-2-Butenyl, 2,3-Dimethyl-3-butenyl, 1-Ethyl-2-butenyl, 1-Ethyl-3-butenyl, 2-Ethyl-1-butenyl, 2-Ethyl-2-butenyl, 2-Ethyl-3-butenyl, 1,1,2-Trimethyl-2-propenyl, 1-Ethyl -1-methyl-2-propenyl and 1-Ethyl-2-methyl-2-propenyl.

As a general rule, $C_3$-$C_6$-alkinyl represents a branched or unbranched hydrocarbon residue with 3 to 6 carbon atoms with one or possibly more triple bonds, which can be substituted if necessary with one or more halogen atom(s)—preferably fluorine—which can be the same as or different from one another.

The following hydrocarbon residues are cited as examples:
2-Propinyl (Propargy), 2-Butinyl, 3-Butinyl, 1-Methyl-2-propinyl, 2-Methyl-2-Propinyl, 2-Pentinyl, 3-pentinyl, 4-Pentinyl, 1-Methyl-2-butinyl, 2-Methyl-2-butinyl, 3-Methyl-2-butinyl, 1-Methyl-3-butinyl, 2-Methyl-3-butinyl, 3-Methyl-3-butinyl, 1,1-Dimethyl-2-propinyl, 1,2-Dimethyl-2-propinyl, 1-Ethyl-2-propinyl, 2-Hexinyl, 3-Hexinyl, 4-Hexinyl, 5-Hexinyl, 1-Methyl-2-pentinyl, 2-Methyl-2-pentinyl, 3-Methyl-2-pentinyl, 4-Methyl-2-pentinyl, 1-Methyl-3-pentinyl, 2-Methyl-3-pentinyl, 3-Methyl-3-pentinyl, 4-Methyl-3-pentinyl, 1-Methyl-4-pentinyl, 3-Methyl-4-pentinyl, 4-Methyl-4-pentinyl, 1,1-Dimethyl-2-butinyl, 1,1-Dimethyl-2-butinyl, 1,1-Dimethyl-3-butinyl, 1,2-Dimethyl-2-butinyl, 1,2-Dimethyl-3-butinyl, 1,3-Dimethyl-2-butinyl, 1,3-Dimethyl-3-butinyl, 2,2-Dimethyl-3-butinyl, 2,3-Dimethyl-2-butinyl, 2,3-Dimethyl-3-butinyl, 1-Ethyl- 2-butinyl, 1-Ethyl-3-butinyl, 2-Ethyl-1-butinyl, 2-Ethyl-2-butinyl, 2-Ethyl-3-butinyl 1,1,2-Trimethyl-2-propinyl, 1-Ethyl-1-methyl-2-propinyl and 1-Ethyl-2-methyl-2-propinyl.

Unless otherwise defined, aryl represents an aromatic mononuclear or polynuclear residue with 4 to 22C– atoms, which can possibly contain one or two heteroatoms. Examples are: Phenyl, Naphthyl, Anthracyl and Pyrol, Furan, Thiophen, Pyridine, Pyridazine, Pyrimidine or Pyrazine, which can be substituted if necessary with one or more halogen atom(s)—preferably fluorine—or which can be substituted one or more times independently from one another by an alkyl group.

Aralkyl means a mononuclear or polynuclear aryl residue in accordance with the above definition, which is bonded to the cationic partial structure by means of a $C_1$-$C_6$-alkyl, $C_3$-$C_6$-alkenyl or a $C_3$-$C_6$-alkinyl bridge, for which the definition of $C_1$-$C_6$-alkyl, $C_3$-$C_6$-akenyl and $C_3$-$C_6$-alkin applies accordingly. For the purpose of the present invention, the benzyl is preferred.

Preferred anions are Bromide, Chloride, Phosphate, Sulphate, Formiate, Acetate, Propionate, Oxalate or Succinate.

The main features of the principle of the sequence of the method according to the invention can be described as follows using a plasmid preparation as an example:

The bacteria are first isolated from the medium containing them, after which, for practical purposes, they are present in the form of a pellet. In the following step, the pellet is resuspended using a resuspension buffer. Resuspension buffers of this kind are known from the state of the art (for example: 50 mM Tris-Cl, pH 8.0, 10 mM EDTA, with RNase A).

The suspension so obtained is mixed with lysis buffer (the lysis buffers that can be used here are likewise known to the person skilled in the art from the state of the art), such as 200 mM NaOH, 1% SDS for example. After lysing, depending on the form it takes, the preparation is neutralised by means of a neutralisation buffer. The neutralisation buffers that can be used here are also familiar to the person skilled in the art in large numbers from the state of the art. They include, for example, buffers such as an aqueous 3 M potassium acetate solution with a pH value of 5.

The resulting reaction mixture is filtered if necessary. Suitable filters are well-known in from the state of the art and are commercially available (such as QIAFILTER® Midi from the company QIAGEN, D-40724 Hilden, for example). The lysate is then mixed with one or more compounds of the general formula (1), preferably in aqueous solution, and after mixing placed on a silica column, preferably a so-called spin column. (Depending on the execution protocol, the compound of the general formula (I) can already be added to the lysis buffer for a "milder lysing". see also Part 4).

If the volume available in the spin column is not sufficient for accommodating the whole amount, an extender in the form of a funnel can be placed on the spin column, which enables the whole quantity of liquid to be accommodated.

The reaction mixture is transported or sucked through the column by applying a vacuum or by centrifuging, whereby the required nucleic acid, here the plasmid DNA, bonds to the surface, preferably to a silica surface.

The column is then washed several times with a wash buffer if necessary. Wash buffers of this kind are also known from the state of the art and include buffers such as "Puffer PE" (QIAGEN, Hilden), for example.

Any wash buffer residue present can be removed from the column material if necessary by means of centrifugation.

Finally, the bonded nucleic acid is eluted from the column with an elution buffer, which is likewise known from the state of the art.

Accordingly, the present invention relates to a method for isolating and cleaning nucleic acids, which can generally be described by the following steps:
lysing a biological sample containing nucleic acid;
if necessary, neutralising the preparation resulting from the lysis;
mixing of the reaction mixture so obtained with one or more compounds of the general formula (I) or their aqueous solution, and bringing the reaction mixture into contact with a silica-based matrix;
washing the nucleic acids;
isolating the nucleic acids.

Furthermore, the present invention relates to the method described above in which an aqueous solution containing 200 mM NaOH and 1 weight-% N SDS is used as a lysis buffer.

Furthermore, the present invention relates to the method described above in which an aqueous 2-3 M potassium acetate solution is used as a neutralisation buffer.

Furthermore, the present invention relates to the method described above in which preferably an aqueous 300 to 1000 mM, particularly preferably a 400 to 800 mM, especially preferably a 500 to mM common salt solution is used as a wash buffer.

Furthermore, the present invention relates to the method described above in which a buffering 70-90% aqueous solution of ethanol with a pH value of 7.5 is used as a wash buffer. Appropriate buffers are known from the state of the art and include, for example, Tris/HCl, MOPS and similar buffer mixtures amongst others.

In addition, the present invention relates to the use of compounds of the general formula (1) for the reversible bonding of nucleic acids to a mineral matrix, wherein the matrix can be made up of a porous and/or non-porous carrier based on metal oxides or metal mix oxides, and can preferably consist of a silicon-oxygen compound, particularly preferably silicon dioxide (silica), or of a silicate or of a glass, silica gel or zeolite.

In addition, the mineral matrix can consist of aluminium oxide, titanium dioxide or zirconium dioxide, or alternatively mixtures of the named metal oxides can be used.

In particular, the present invention relates to the use of compounds of the general formula (I) for the bonding of nucleic acids, wherein these can be present in the form of single and/or double-stranded DNA and/or RNA as well as single nucleotides and/or ribonucleotides, and, in the case of DNA, the DNA is namely genomic DNA, plasmid DNA, and/or plastid DNA, and, in the case of RNA, the RNA is mRNA, tRNA, rRNA and/or sn-RNA.

Finally, the present invention relates to a kit for the isolation and/or cleaning of nucleic acids, at least containing a compound of the general formula (I).

EXAMPLES

The present invention is henceforth exemplified by means of the following examples:

The following abbreviations are used:
CTAB Cetyltrimethylammonium bromide
  Hexadecyltrimethylammonium bromide
TTAB Tetradecyltrimethylammonium bromide
DoTAB Dodecyltrimethylammonium bromide
DTAB Decyltrimethylammonium bromide
OTAB Octcyltrimethylammonium bromide
GEL Yield determined by a densitometric evaluation of an agarose gel
min minute(s)
Buffer PE Commercially available wash buffer (QIAGEN, D-40724 Hilden)
Buffer EC Commercially available buffer for use in cell culture
  (QIAGEN, D-40724 Hilden)
Buffer RLT Commercially available lysing/bonding buffer (QIAGEN, D-40724 Hilden)
Buffer EB Commercially available elution buffer (QIAGEN, D-40724 Hilden)
Buffer DP3 Commercially available neutralisation buffer (QIAGEN, D-40724 Hilden)
Buffer S3 Commercially available neutralisation buffer (QIAGEN, D-40724 Hilden)
Buffer CE3 Commercially available extraction buffer (QIAGEN, D-40724 Hilden)
OD Yield determined by means of photometric measurement at 260 nm
  (optical density)
RT Room temperature (ca. 20-25° C.)
X Mean value of multiple determinations Part 1: Cleaning and Isolation of Nucleic Acids Using Cationic Detergents Unless stated otherwise, Examples 1 to 4 were carried out in accordance with the following protocol:

Protocol (1) for plasmid DNA preparations from *E.coli* on a "medium scale":
1. Resuspend bacteria pellet in 2 ml resuspension buffer;
2. Add 2 ml lysis buffer—then lyse for ca. 3 min;
3. Add 2 ml neutralisation buffer, mix by inverting;
4. Transfer immediately to a QIAFILTER® Midi, incubate for 3 min at RT and filter;
5. Place 10 ml extender on the spin column and position on QIAVAC®;
6. Add 2 ml of the detergent solution to the lysate, mix thoroughly and place on the column;
7. Suck the mixture through, remove the vacuum;
8. Discard the extender;
9. Place spin column in collection tube;
10. Optional washing of the membrane by adding 750 µl salt buffer, centrifuge for 1 min at 14,000 rpm;
11. Wash the membrane by adding 750 µl buffer PE, centrifuge for 1 min at 14,000 rpm;
12. Centrifuge once more for 1 min at 14,000 rpm to remove buffer residues;
13. Place spin column on 1.5 ml Eppendorf tube;
14. Elute with 200 µl buffer EB. Pipette onto the membrane, incubate for 1 min and centrifuge (1 min at 14,000 rpm).

Example 1

Comparison of the Bonding Chemistry According to the Invention Using Detergents Compared with so-Called "Alcoholic" Bonding Chemistry In accordance with the present protocol (1), 25 ml of a DH5α/pCMVβ culture (high-copy plasmid) were precipitated with 2 ml, 2.5 ml and 4 ml respectively of a detergent solution (4 weight-% in 0.5 M NaCl) or with isopropanol: Tables 1 and 2

| CTAB bond, yields $OD_{260}$ (µg) | | | |
| --- | --- | --- | --- |
|   | 2 ml | 2.5 ml | 4 ml |
| 1 | 448 | 460 | 502 |
| 2 | 453 | 532 | 379 |
| X | 450 | 491 | 440 |

| iso-Propanol bond, yields $OD_{260}$ (µg) | | | |
| --- | --- | --- | --- |
|   | 2 ml | 2.5 ml | 4 ml |
| 1 | 331 | 439 | 716 |
| 2 | 325 | 381 | 679 |
| X | 328 | 410 | 698 |

Tables 3 and 4

| CTAB bond, yields GEL (µg) | | | |
| --- | --- | --- | --- |
|   | 2 ml | 2.5 ml | 4 ml |
| 1 | 421 | 456 | 384 |
| 2 | 421 | 464 | 357 |
| X | 421 | 460 | 370 |

| CTAB bond, yields GEL (µg) | | | |
| --- | --- | --- | --- |
|   | 2 ml | 2.5 ml | 4 ml |
| 1 | 308 | 428 | 354 |
| 2 | 374 | 374 | 352 |
| X | 341 | 401 | 353 |

As the above data show, the detergent bonding system has a greater stability compared with an alcohol-based bond for the same to higher yields.

Example 2

Control of the Bond and Selectivity by Means of the Salt Concentration

In the present example, 25 ml in each case of a DH5α/pBRCMVβ culture (low-copy plasmid) were bonded with CTAB at different salt concentrations in accordance with protocol (1).

The mean values of a double determination are reproduced in each case in Tables 5 and 6 below:

| CTAB bond, yields OD260 (µg) | | | | | | |
|---|---|---|---|---|---|---|
| 0.4M | 0.5M | 0.6M | 0.7M | 0.8M | 0.9M | 1.0M |
| 40 | 26 | 21 | 12 | 14 | 11 | 220 |

| CTAB bond, yields GEL (µg) | | | | | | |
|---|---|---|---|---|---|---|
| 0.4M | 0.5M | 0.6M | 0.7M | 0.8M | 0.9M | 1.0M |
| 9 | 8 | 11 | 9 | 14 | 8 | 0 |

The experimental results clearly show that optimum conditions for the selected bonding of a required nucleic acid can be set by choosing a suitable salt concentration. Furthermore, the identical values of the photometric and densitometric determination for a concentration of 0.8 M NaCl provide evidence that only the required plasmid DNA is to be found in the respective preparation.

Example 3

Use of Wash Buffer Containing Salt for Removing RNA Contamination

If the cationic detergents are considered as "soluble anionic exchangers", it should be possible by means of a step gradient to remove unwanted nucleic acids after bonding to the membrane and thus to obtain an additional selectivity of bonding.

In the example shown, 50 ml in each case of a DH5α/pBRCMVβ culture (low-copy plasmid) were bonded to the membrane with 1% CTAB in 0.8 M NaCl in accordance with protocol (1). The bonded DNA was then washed with a wash buffer of different common salt concentrations (optional Step 10 in protocol (1)):
a) No optional washing step
b) 300 mM NaCl
c) 600 mM NaCl
d) 800 mM NaCl
Tables 7 and 8

| CTAB bond, yields OD$_{260}$ (µg) | | | | |
|---|---|---|---|---|
| | a) | b) | c) | d) |
| 1 | 122 | 60 | 23 | 1.7 |
| 2 | 97 | 76 | 43 | 1.4 |
| X | 110 | 68 | 33 | 1.5 |

| CTAB bond, yields GEL (µg) | | | | |
|---|---|---|---|---|
| | a) | b) | c) | d) |
| 1 | 47 | 28 | 19 | 0.2 |
| 2 | 47 | 41 | 48 | 0.4 |
| X | 47 | 35 | 34 | 0.3 |

Figure 1:
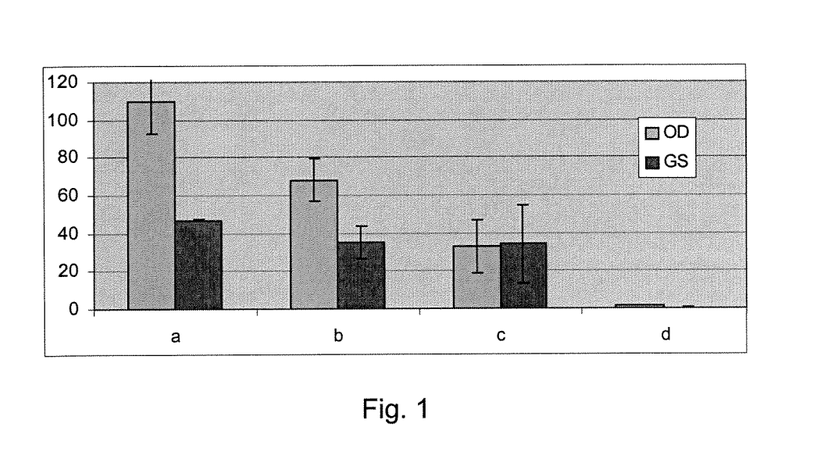
FIGS. 1-11 are graphics and pictorials showing results from the examples provided herein.

The experimental data shown in the above tables are reproduced in graphical form in FIG. 1. The result shows that the detergent nucleic acid complexes on the membrane behave in the same way as nucleic acids, which are bonded to an anion exchanger. Contamination can therefore be selectively removed by using a wash buffer with suitable salt concentration.

Further, it has been shown that with all the detergents specified above with a chain length of more than eight carbon atoms, plasmid DNA of identical purity (OD/GEL values practically identical) can be bonded to a silica membrane. At the same time, the yields depend on the detergent used and the salt concentrations used (ion strengths) of the solution.

Here, it has been shown that bonding also takes place at low salt concentrations at which no inhibition of DNA precipitation occurs.

Example 4

Quality of the Isolated DNA

To assess the quality of the isolated DNA, comparisons were carried out between alcoholic bonding chemistry and bonding with a cationic detergent. The results are shown in the following Tables 9 and 10:
a) Examination for endotoxin contamination (EU/µg DNA):

| high-copy plasmid: | | |
|---|---|---|
| | iso-Propanol | CTAB |
| 1 | 1241 | 3 |
| 2 | 1466 | 11 |
| X | 1354 | 7 |

| low-copy plasmid (without additional washing step): | | |
|---|---|---|
| | iso-Propanol I | CTAB |
| 1 | 2395 | 15 |
| 2 | 2536 | 19 |
| X | 2466 | 17 |

While the endotoxin content when using alcoholic bonding chemistry lies in the usual range for DNA preparations by means of silica technology, the contamination in the case of CTAB preparations lies in a range, which is normally only achieved using anion exchanger columns.

b) Results of the transfection in endotoxin-sensitive cells (Huh7):

Tranfections are critical applications for which the plasmid DNA used must be as free as possible from contamination (in particular endotoxins).

The cells were transfected according to the SuperFect protocol (QIAGEN, D-40724 Hilden). The plasmid isolated by means of an anion exchanger column (Ultrapure100, QIAGEN, D-40724 Hilden) was used as a reference (100%).

Figure 2:
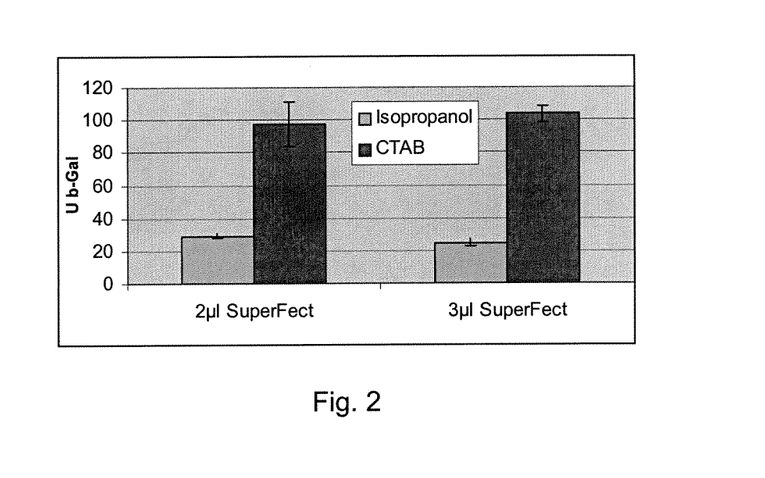

The results achieved are shown in FIG. 2.

The results of the transfection showed values of ca. 100% for the DNA isolated with CTAB, i.e. identical to the preparations with an anion exchanger column (Ultrapure 100).

On the other hand, preparations with iso-propanol bonding gave significantly worse transfection results consistent with the high endotoxin values (see above).

Part 2: Omission of Prior Clarification of the Cell Lysate

Unless stated otherwise, Examples 5 to 8 were carried out in accordance with the following protocol:

Protocol (2) for a quick preparation of plasmid DNA from *E. coli* on a "small-scale" (for 1.5 ml bacteria culture):
1. Resuspend bacteria pellet in 150 ml resuspension buffer;
2. Add 150 µl lysis buffer. Lyse for ca. 3 min;
3. Add 150 ml neutralisation buffer, mix by inverting;
4. Add 300 ml of the detergent solution to the lysate, mix thoroughly and place on the column;
5. Centrifuge (1 min at 14,000 rpm);
6. Wash by adding 750 µl buffer PE, centrifuge for 1 min at 14,000 rpm.
7. Centrifuge once more for 1 min at 14,000 rpm to remove buffer residues.
8. Place spin column on 1.5 ml Eppendorf tube;
9. Elute with 100 µl buffer EB. Pipette onto the membrane, leave for 1 min and centrifuge (1 min at 14,000 rpm).

Example 5

Optimisation of the Bond when Omitting Lysate Clarification

In the present example, 1.5 ml in each case of a DH5α/pBRCMVβ culture (high-copy) were bonded with CTAB at different salt concentrations in accordance with protocol (2).

The mean values of a double determination are given in each case.

The required salt concentration in the detergent solution was optimised based on the results with lysate clarification: 300 µl of a 1% CTAB solution with the specified salt concentration were used in each case.

Figure 3:
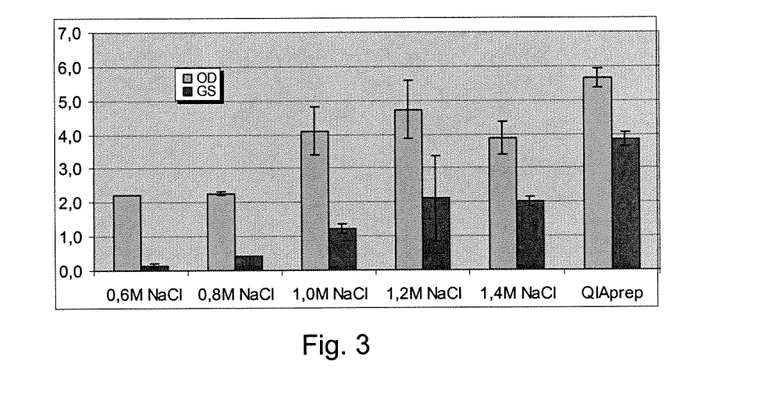

As can be seen from FIG. 3, the best results were obtained with 1.2 and 1.4 M NaCl. It should be noted here that no further bonding takes place with lysate clarification at these salt concentrations. In contrast to this, 0.8 M NaCl, the determined optimum for lysate clarification (cf. Example 2), led in this case to considerably worse results.

Example 6

Preparation in the Spin Format

In the present example, 1.5 ml in each case of a DH5α/pCMVβ culture (high-copy) were precipitated with 1% CTAB in 1.2 M NaCl or isopropanol in accordance with protocol (2).

Buffer DP3 (3 M ammonium acetate, pH 5.5) and buffer S3 (2M potassium acetate, pH 5.5) were used in each case as a neutralisation buffer. A QIAPREP® preparation from the company QIAGEN GmbH was used as an additional comparison.

Figure 4:
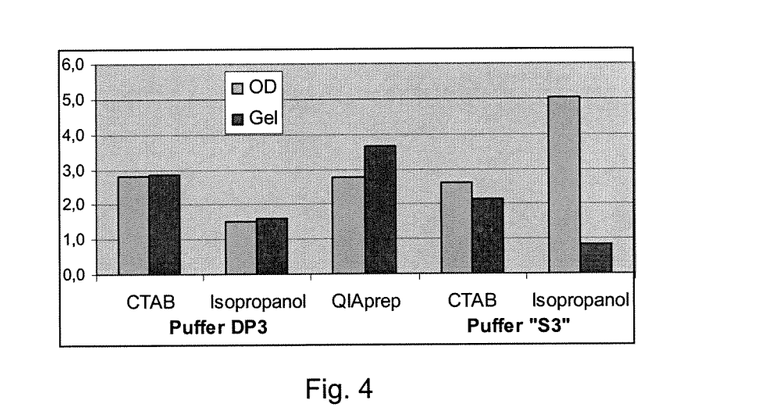

As FIG. 4 shows, double the yield is obtained with the cationic detergent CTAB than when isopropanol is used. The preparations with the buffer S3 showed only slightly lower yields for the cationic bonding and, as before, a good correspondence between OD and GEL. In contrast with this, there was a very high over-quantification in the OD when using isopropanol.

Example 7

Preparation in the 96-Well Format, Automated

In the present example, a shaking flask cultivation of DH5α/pCMVβ culture (high-copy) was distributed in a 96-well plate in the form of 1.5 ml aliquots.

One 96-well plate at a time was subsequently prepared on an analysing robot (e.g. the BR8000/QIAGEN GmbH) with CTAB or isopropanol to form a DNA bond.

The latest DP96 protocol was chosen for isolating with isopropanol (in each case 100 µl of the lysis buffer, 180 µl isopropanol; so-called "low-volume protocol"). For isolation with CTAB, a protocol version was chosen, which was as close as possible to the previously used spin protocol (in each case 150 µl lysis buffer, 300 µl CTAB solution).

The yield per $OD_{260}$ was determined for all 96 wells, (see Tables 11 and 12). In addition, a densitometric analysis of an agarose gel was carried out for seven wells at a time in order to determine the yield.

Figure 5:
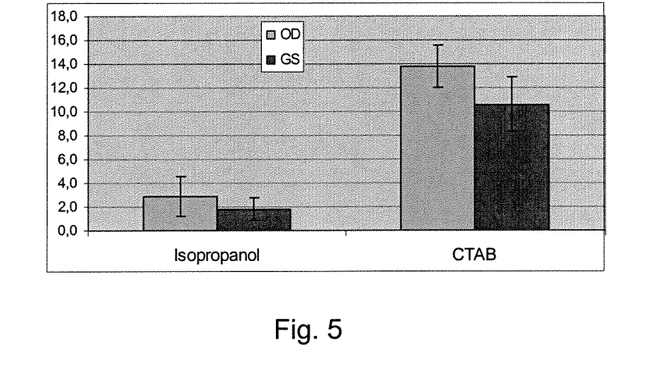

FIG. 5 shows the comparison of OD and GEL for seven randomly chosen wells. The advantage of the new bonding chemistry can be clearly seen in the yield for the selected range. The correspondence between OD and GEL is equally good in both cases.

The difference is less obvious with the values in Tables 11 and 12 below, which were determined over all 96 wells, than with the seven selected samples, but is still ca. 2-3 times higher.

CTAB:

| | $OD_{260}$: | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 15.0 | 4.0 | 13.4 | 15.4 | 13.1 | 11.4 | 12.0 | 11.4 | 11.7 | 8.0 | 8.0 | 6.4 |
| B | 14.8 | 16.9 | 15.4 | 14.9 | 7.7 | 10.2 | 10.9 | 14.7 | 10.8 | 7.1 | 7.6 | 9.1 |
| C | 12.0 | 13.4 | 9.0 | 13.2 | 12.3 | 12.3 | 8.6 | 10.3 | 6.4 | 9.2 | 10.7 | 8.7 |
| D | 14.0 | 13.9 | 9.2 | 16.2 | 12.9 | 11.1 | 11.3 | 11.9 | 11.6 | 9.1 | 8.7 | 6.9 |
| E | 12.7 | 14.9 | 15.1 | 11.2 | 11.2 | 12.3 | 9.3 | 12.0 | 9.3 | 9.0 | 9.8 | 11.0 |
| F | 14.5 | 14.2 | 12.0 | 8.6 | 11.8 | 12.0 | 16.4 | 11.7 | 10.0 | 11.6 | 7.1 | 3.4 |
| G | 15.9 | 14.9 | 19.6 | 12.2 | 13.9 | 13.7 | 14.9 | 14.5 | 10.4 | 7.4 | 8.4 | 11.6 |
| H | 15.0 | 9.3 | 11.5 | 13.3 | 8.9 | 8.7 | 13.4 | 11.3 | 13.1 | 6.0 | 10.2 | 11.9 |

Average: 11.4 µg

Isopropanol:

| | $OD_{260}$: | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 2.8 | 4.1 | 5.0 | 3.4 | 3.6 | 1.6 | 3.1 | 2.5 | 0.5 | 2.6 | 0.4 | 0.03 |
| B | 4.7 | 4.2 | 4.5 | 3.5 | 3.4 | 5.0 | 4.3 | 4.0 | 4.7 | 3.8 | 3.2 | 3.1 |
| C | 3.5 | 4.2 | 5.3 | 4.9 | 4.7 | 1.9 | 1.9 | 4.2 | 4.5 | 4.8 | 3.5 | 1.7 |
| D | 4.2 | 4.5 | 4.5 | 3.7 | 2.8 | 4.1 | 4.4 | 4.3 | 1.9 | 4.4 | 3.1 | 4.2 |
| E | 4.8 | 5.8 | 5.9 | 5.5 | 4.6 | 5.0 | 3.7 | 4.5 | 4.2 | 3.9 | 4.5 | 4.6 |
| F | 5.1 | 4.9 | 4.7 | 4.8 | 2.8 | 4.8 | 4.6 | 3.9 | 2.7 | 5.4 | 5.0 | 4.0 |

-continued

| | | | | | OD$_{260}$: | | | | | | | |
|---|---|---|---|---|---|---|---|---|---|---|---|---|
| | 1 | 2 | 3 | 4 | 5 | 6 | 7 | 8 | 9 | 10 | 11 | 12 |
| G | 4.8 | 4.8 | 5.2 | 6.1 | 3.9 | 3.4 | 4.3 | 6.4 | 4.6 | 4.0 | 5.0 | 2.4 |
| H | 4.0 | 5.5 | 6.9 | 4.2 | 3.9 | 4.4 | 5.2 | 4.8 | 5.3 | 3.8 | 3.2 | 4.0 |

Average: 4.0 µg

Example 7

Quality of the DNA Obtained

Figure 6:
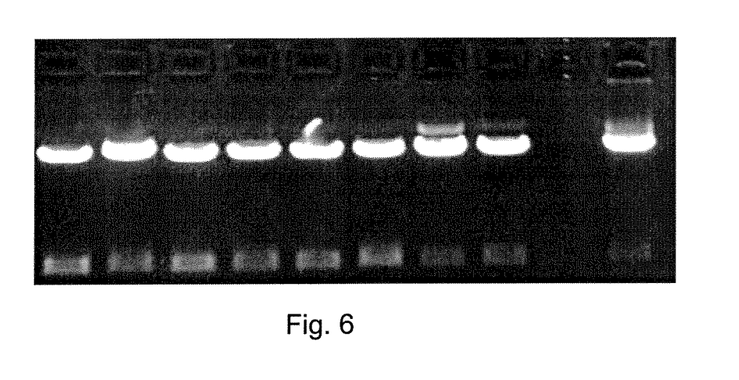

Different applications were carried out to determine the quality of the isolated DNA:
a) Restriction Analysis
The samples of the isolated plasmid DNA in Example 7 were digested with a salt-sensitive restriction enzyme. As a check, the same plasmid was used, but which had first been isolated using an anion exchanger column (e.g. a UP100/ QIAGEN GmbH).
FIG. 6 clearly shows that all digested samples have the expected additional bands at 0.7 kb. No difference from the check sample could be detected.
b) Sequencing Capability
As can be seen from Table 13 below, all DNA samples used have a very good read length averaging approximately 800 bp. The signal strength of the individual bases and the early start of readability also show that the quality of the isolated plasmid DNA is very well suited for sequencing.

| Name | G | A | T | C | Start | Stop | Read length |
|---|---|---|---|---|---|---|---|
| A942_a_P1.ab1 | 990 | 1205 | 1173 | 1533 | 21 | 838 | 817 |
| A942_b_P1.ab1 | 691 | 856 | 822 | 1117 | 20 | 803 | 783 |
| A942_c_P1.ab1 | 823 | 1009 | 1014 | 1348 | 20 | 804 | 784 |
| A942_d_P1.ab1 | 1158 | 1525 | 1379 | 1907 | 21 | 731 | 710 |
| A942_e_P1.ab1 | 1230 | 1580 | 1481 | 2049 | 21 | 808 | 787 |
| A942_f_P1.ab1 | 1197 | 1507 | 1539 | 2030 | 16 | 808 | 792 |
| A942_g_P1.ab1 | 1136 | 1560 | 1627 | 2247 | 21 | 822 | 801 |
| A942_h_P1.ab1 | 1101 | 1326 | 1223 | 1620 | 21 | 808 | 787 |
| A942_i_P1.ab1 | 1094 | 1334 | 1360 | 1771 | 19 | 840 | 821 | c) Determination of the Endotoxin Content:
The endotoxin content of the samples in series 4 was determined by means of the LAL Kinetic Kit (Cambrex).
Endotoxin Units/µg of DNA Used:

| | A | B | C | D | E | F | G | H | Average |
|---|---|---|---|---|---|---|---|---|---|
| Series 4 | 2442 | 2420 | 778 | 2230 | 1242 | 1329 | 1968 | 1833 | 1780 |

The measurement gave endotoxin contamination levels of the same order of magnitude as a conventional silica preparation with chaotropic bonding chemistry (cf. Example 4)
In contrast with this, the values for alcoholic bonding chemistry without lysate clarification were approximately a factor of 10 higher.
Conclusion:
As Examples 5 to 7 show, in a similar way to alcoholic bonding chemistry (see also WO 03/040364), the new bonding chemistry also allows lysate clarification to be omitted, which above all is a great advantage with regard to high-throughput applications or automated systems.
As Example 6 shows, the automated protocol (2) can very easily be accommodated by existing systems. Compared with alcoholic bonding chemistry, cationic bonding chemistry produces plasmid DNA, which, with regard to quality, is the same or better—with considerably higher yields.
Part 3: Subsequent Cleaning of DNA
Some examples relating to the cleaning of DNA of any size are given below. In doing so, the separation of free nucleotides or primers after enzymatic reactions, and the selective isolation of primers as well as larger DNA molecules were targeted.
Unless stated to the contrary, Examples 9 to 11 were carried out in accordance with the protocol (3) below, which shows the sequence of subsequent cleaning with cationic detergents for bonding to a silica membrane on a small scale.
Protocol (3) for the selective bonding of DNA depending on the size
1. Mix sample with detergent solution;
2. Mix well and place on the column;
3. Centrifuge (1 min at 14,000 rpm);
4. Wash by adding 750 µl buffer PE, centrifuge for 1 min at 14,000 rpm.
5. Centrifuge once more for 1 min at 14,000 rpm to remove buffer residues.
6. Place spin column on 1.5 ml Eppendorf tube;
7. Elute with 100 µl buffer EB. Pipette onto the membrane, leave for 1 min and centrifuge (1 min at 14,000 rpm).
The given Examples 9 to 11 demonstrate three different parameters, which can be utilised to differentiate the bonding of different DNA molecules:
Amount of detergent used
pH value
Ions contained in the bonding preparation (cations)
These three parameters should provide sufficient combination options to be able to easily achieve any required selectivity.

Example 9

Selective Bonding of a 100 bp Fragment

Figure 7:
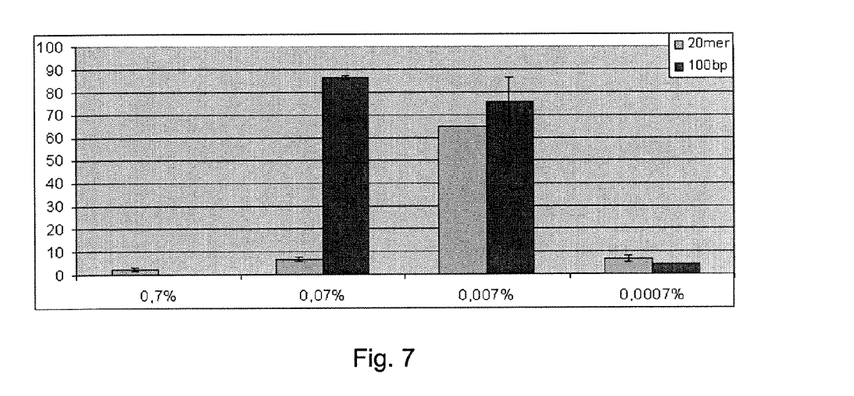

2 µg 100 bp fragment or 20mer in each case were dissolved in 50 µl buffer EB, mixed with different dilutions of a TTAB solution (300 µl in each case) and further treated in accordance with the protocol (3) described above.
The result shown in FIG. 7 shows that an almost quantitative depletion of the 20mer can be achieved solely due to the amount of detergent used (here: 0.07%).

Example 10

Figure 8:
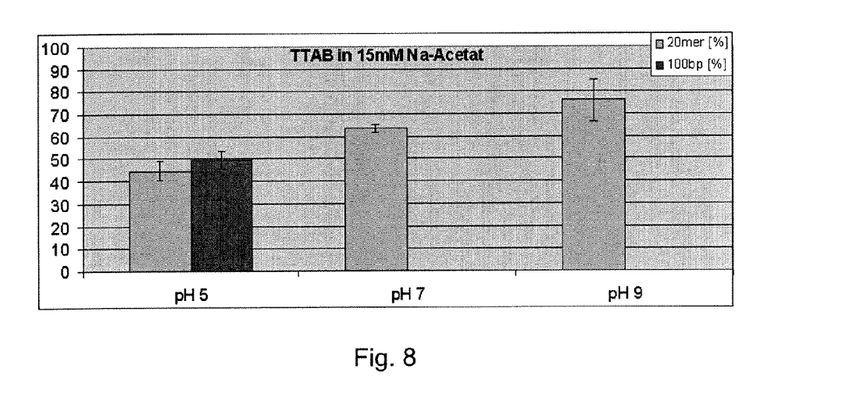

Selective Bonding of a 20 Mer Oligonucleotide by the Choice of a Suitable pH Value 1 µg of a 20mer or 100 bp fragment in each case were dissolved in 100 µl buffer EB (10 mM Tris/HCl, pH 8.5) and mixed with 300 µl of a 0.05% acetate buffered TTAB solution (15 mM acetic acid/Na acetate, pH value 5; 7 and 9).
The samples were further treated in accordance with the protocol (3) described above.
The result shown in FIG. 8 shows a recovery and therefore bonding of both the 20mer and the 100 bp fragment at pH5. In contrast with this, only the 20mer was bonded at higher pH values. This shows that, by means of the bonding chemistry according to the invention, a required separation of DNA fragments can be achieved solely through the selection of a suitable pH value.

Example 11

Selective Bonding or Non-Bonding of a 100 bp Fragment by Choosing a Suitable Cation 2 µg of a 20mer or 100 bp fragment or pUC21 plasmid in each case were dissolved in 50 µl buffer EB (10 mM Tris/HCl, pH 8.5) and mixed with 50 µl of the appropriate acetate solution (see list a to d below) with a pH value of about 5.5. To this were added 50 µl of a 4% CTAB solution in 500 mM NaCl and further treated in accordance with the protocol (3) described above.
  a) 2 M potassium acetate
  b) 1 M magnesium acetate
  c) 1 M calcium acetate
  d) 1 M manganese(II) acetate
Whereas the 20mer was separated in every case, the plasmid pUC21 remained bonded each time. The 100 bp fragment could be bonded or not bonded depending on the cation used.

Figure 9:
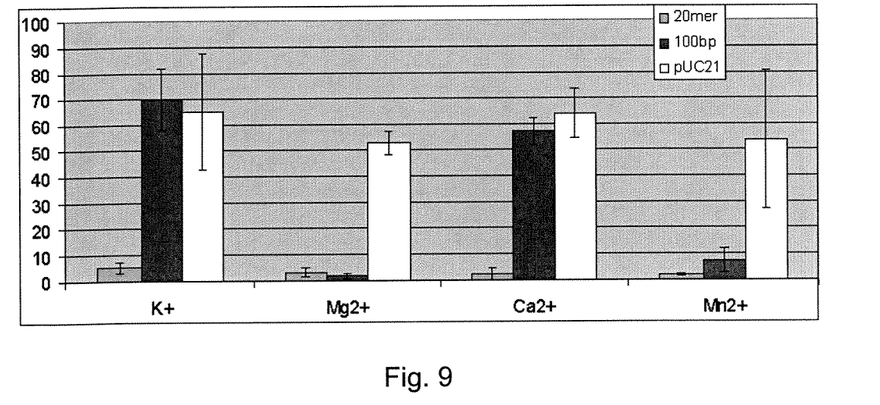

FIG. 9 therefore shows that a certain selectivity can be achieved for the required DNA molecules solely through the choice of the cation used.

Part 4: Isolation of RNA (Incl. DNA and Native Proteins)

In the following, it will be shown how the new bonding chemistry can also be used to isolate RNA from biological material. Here, the lysis takes place by means of a normal mild lysis buffer, such as has long been used for isolating proteins, for example. According to the invention, however, this buffer contains the cationic detergent, which on the one hand stabilises the RNA, and on the other promotes bonding to the silica membrane.

With this method, all nucleic acids are bonded in the initial bonding step, and these are then selectively eluted one after the other with already known buffers.

In contrast with the known conventional methods, in which the DNA is stabilised by inactivating the RNases with high concentrations of chaotropic salts, in the case of bonding to cationic detergents, the RNA is protected from attack. This means that the proteins present in the sample retain their biological function and can be further processed in native form from the breakthrough of the silica spin column.

This provides quite significant advantages compared with the previously known systems, in which the sample must be divided, the one half being used for the isolation of native proteins with simultaneous RNA degradation, and the second half being used for the isolation of nucleic acids with simultaneous denaturing of the proteins, which along with the disadvantage that half of the samples have to be thrown away in each case, can very easily lead to falsified results when inhomogeneous sample material is divided.

With the method according to the invention, it is also possible for the first time to carry out functional studies on the RNA and protein level from one and the same sample.

Advantageously, the genomic DNA can also be isolated, which can be of great importance in analyses, in which observations are checked for their causes in the genetic background (mutations).

Unless stated otherwise, Examples 12 and 13 below were carried out in accordance with the following protocol:
Protocol (4) for the isolation of RNA, gDNA and native proteins from a sample
  (Protocol for a 12-Well Cell Culture Format)
  1. Remove medium and wash cells with 1 ml buffer EC;
  2. Cool plate on ice for 5 min;
  3. Mix cells with 400 µl lysis buffer (1.6 vol extraction buffer CE 3 + 1 vol 8% TTAB in water) and allow to stand for 5 min at room temperature. (Any buffer, which is commonly used for the isolation of native proteins, can be used as the basis of the lysis buffer, which is then mixed with a suitable amount of a cationic detergent.)
  4. Scrape off the cells and homogenise the lysate by pipetting up and down 3×;
  5. Centrifuge the lysate using a commercially available spin column (e.g. an RNEASY® spin column / QIAGEN GmbH).
  6. The protein fraction, which is subsequently analysed separately, is to be found in the breakthrough.
  7. The spin column, which is loaded with the nucleic acid obtained, is rinsed with 350 µl of a commercially available chaotropic buffer (e.g. RLT buffer / QIAGEN GmbH);
  8. The breakthrough is collected and further treated in step 10.
  9. The spin column is subsequently washed with PE buffer and the gDNA remaining on the column is eluted with EB buffer.
  10. Mix the RLT breakthrough containing the RNA with 250 µl 100% ethanol;
  11. Centrifuge using a new RNEASY® spin column
  12. and isolate the required RNA, for example with the "RNEASY® Mini Protocol for Isolation of Total RNA from Animal Cells" Step 4, P. 32 from the RNEASY® Mini Handbook, QIAGEN GmbH / Status Jun. 2001.

Example 12

Isolation of RNA and DNA

HeLa S3 cells were cultivated in the 12-well cell culture format and four wells in each case were lysed with two different common protein lysis buffers (see list a and b) and CTAB as a detergent. Appropriate RNEASY® preparations were used as a reference c) (QIAGEN GmbH).
  a) β-G galactosidase lysis buffer (see below) with 1% CTAB in 100 mM NaCl (final concentration 188 mM)
  b) Cell extraction buffer CE3 with 1% CTAB in 300 mM NaCl (final concentration 804 mM)
  c) RNEASY® (QIAGEN) β-galactosidase lysis buffer: 10 mM Tris, pH 7.4
  1 mM EDTA
  100 mM NaCl
  5 mM $MgCl_2$
  1% NP40
The RNA and gDNA were then isolated in accordance with the protocol (4) described above.

Figure 10:
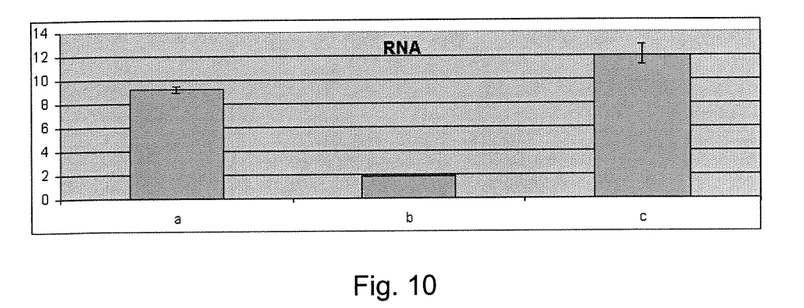
Figure 11:
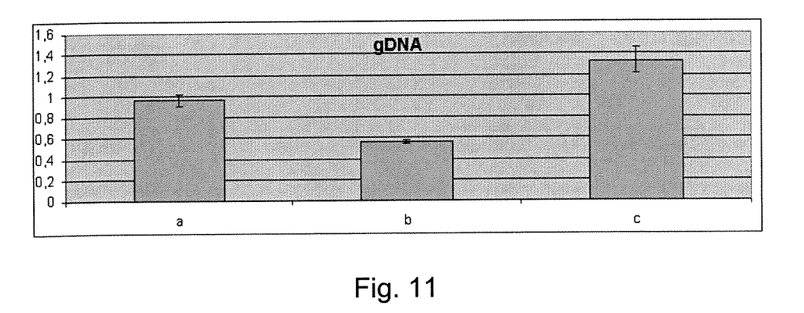

The results shown in FIGS. 10 and 11 clearly show, particularly in the comparison of preparations a) and c), that RNA and DNA can be isolated simultaneously with the method according to the invention in combination with the already known buffers. The yield and quality here are comparable with the established systems.

An optimisation of the NaCl concentration for the lysis buffer CE3 to a final 375 mM carried out during the development subsequently also led to comparable results.

Example 13

Quality of the Isolated Proteins

HeLa S3 cells were cultivated in the 12-well cell culture format and transfected with a plasmid carrying the β-galactosidase gene. After 48 hours, the cells were lysed in accordance with the protocol (4) described above, four wells in each case being mixed with two different common protein lysis buffers (see list a and b).

The lysis with a standard lysis buffer as used in β-galactosidase activity measurements was used as a reference.
a) Lysis buffer with 3% TTAB
b) Lysis buffer with 3% TTAB, subsequently centrifuged using RNeasy spin column
c) Standard β-galactosidase lysis buffer (composition see Example 12)

The protein fraction was then mixed with a volume of a 3% SDS solution in order to precipitate the TTABs. The activity of the enzyme was measured before and after the SDS precipitation.

As has been demonstrated by the yellow colouring of the reaction solutions with β-galactosidase in the wells (not shown), the proteins obtained continue to be biologically active. This is not possible with methods adequately known from the state of the art, which work with highly molar chaotropic and thus strongly denaturising buffers, which have an RNase inactivation as their objective.

The invention claimed is:

1. Method for isolating and cleaning nucleic acids from a lysate, comprising
a) lysing a biological sample containing nucleic acid with a lysis buffer;
b) optionally neutralizing the preparation resulting from the lysis with a neutralisation buffer;
c) mixing a reaction mixture so obtained with one or more compounds of formula (I):

$$Y^+R_1R_2R_3R_4X^- \quad (I)$$

where
Y is nitrogen or phosphorus
$R_1$, $R_2$, $R_3$ and $R_4$ are independently from one another an unbranched or branched $C_1$-$C_{20}$-alkyl residue, $C_3$-$C_6$-alkenyl residue, $C_3$-$C_6$-alkinyl residue and/or a $C_6$-$C_{20}$-aryl residue as well as a $C_6$-$C_{26}$-aralkyl residue, and X— is an anion of an inorganic or organic single or multi-basic acid or their aqueous solution,
and brought into contact with a mineral matrix, wherein the nucleic acids bind to the mineral matrix in the presence of the one or more compounds of formula I,
d) washing nucleic acids with a wash buffer; and
e) isolating nucleic acids, and
wherein the compound of formula (I) promotes binding to the matrix.

2. Method according to claim 1, wherein $R_1$ is a higher alkyl residue, $R_2$, $R_3$ and $R_4$ each is a methyl group, and Y is nitrogen.

3. Method according to claim 1, wherein $R_1$ is an aralkyl residue, $R_2$ is a higher alkyl residue, and $R_3$ and $R_4$ are each a methyl group.

4. Method according to claim 1, wherein X⁻ is Bromide, Chloride, Phosphate, Sulphate, Formiate, Acetate, Propionate, Oxalate or Succinate.

5. Method according to claim 1, wherein an aqueous solution containing 200 mM NaOH and 1 weight-%/V SDS is used as a lysis buffer.

6. Method according to claim 1, wherein a 2-3 M aqueous potassium acetate solution is used as a neutralisation buffer.

7. Method according to claim 1, wherein an aqueous 300 to 1000 mM, common salt solution is used as a wash buffer, and/or a buffering 70-90% aqueous ethanol solution, with a pH value of 7.5 is used as a wash buffer.

8. A method for bonding nucleic acids to a mineral matrix comprising obtaining at least one compound of the formula (I):

$$Y+R_1R_2R_3R_4X^- \quad (I)$$

wherein
Y is nitrogen or phosphorus
$R_1$, $R_2$, $R_3$ and $R_4$ are independently from one another an unbranched or branched $C_1$-$C_{20}$-alkyl residue, $C_3$-$C_6$-alkenyl residue, $C_3$-$C_6$-alkinyl residue, a $C_6$-$C_{20}$-aryl residue, and/or a $C_6$-$C_{26}$-aralkyl residue, and
X– is an anion of an inorganic or organic single or multi-basic acid and reversibly bonding said nucleic acids to said mineral matrix using said compound, wherein reversible bonding of said nucleic acids to said matrix occurs in the presence of the one or more compound of formula I and wherein the compound of formula (I) promotes binding to the matrix.

9. A method according to claim 8, wherein $R_1$ is a higher alkyl residue, $R_2$, $R_3$ and $R_4$ each are a methyl group, and Y is nitrogen.

10. A method according to claim 8, wherein $R_1$ is an aralkyl group, $R_2$ is a higher alkyl residue, and $R_3$ and $R_4$ each are a methyl group.

11. A method according to claim 8 wherein X is Bromide, Chloride, Phosphate, Sulphate, Formiate, Acetate, Propionate, Oxalate or Succinate.

12. A method according to claim 8, wherein the mineral matrix comprises a porous and/or a non-porous carrier based on metal oxides and/or metal mix oxides.

13. A method according to claim 12, wherein the mineral matrix comprises a silicon-oxygen compound or a silicate.

14. A method according to claim 12, wherein the mineral matrix comprises glass, silica gel and/or a zeolite.

15. A method according to claim 12, wherein the mineral matrix comprises aluminium oxide, titanium dioxide and/or zirconium dioxide.

16. A method according to claim 15, wherein a mixture of a metal oxides is used.

17. A method according to claim 8, wherein said nucleic acids comprise single and/or double-stranded DNA and/or RNA, and/or single nucleotides and/or ribonucleotides.

18. A method according to claim 17, wherein the DNA is genomic DNA, plasmid DNA and/or plastid DNA.

19. A method according to claim 17, wherein the RNA is mRNA, tRNA, rRNA and/or sn-RNA.

20. A kit capable of isolating and/or cleaning nucleic acids according to the method of claim 1, said kit comprising:
a compound of formula (I)

$$Y^+R_1R_2R_3R_4X^- \quad (I)$$

wherein
Y is nitrogen or phosphorus
$R_1$, $R_2$, $R_3$ and $R_4$ are independently from one another an unbranched or branched $C_1$-$C_{20}$-alkyl residue, $C_3$-$C_6$-alkenyl residue, $C_3$-$C_6$-alkinyl residue and/or a $C_6$-$C_{20}$-aryl residue, and/or a $C_6$-$C_{26}$-aralkyl residue, and
X– is an anion of an inorganic or organic single or multi-basic acid, and
wherein said compound optionally present in aqueous solution;
optionally a lysis buffer,
optionally a neutralisation buffer,
optionally a wash buffer,
optionally an elution buffer, and a mineral matrix, which can bond nucleic acids, wherein said compound of formula (I) promotes binding to said matrix when said kit is in use.

21. Kit according to claim 20, wherein $R_1$ is a higher alkyl residue, $R_2$, $R_3$ and $R_4$ each are a methyl group, and Y represents nitrogen.

22. Kit according to claim 20, wherein $R_1$ is an aralkyl residue, $R_2$ is a higher alkyl residue, and $R_3$ and $R_4$ each are a methyl group.

23. Kit according to claim 20, wherein X is Bromide, Chloride, Phosphate, Sulphate, Formiate, Acetate, Propionate, Oxalate or Succinate.

* * * * *